US006953588B2

(12) United States Patent
Cooper et al.

(10) Patent No.: US 6,953,588 B2
(45) Date of Patent: *Oct. 11, 2005

(54) MULTI-VITAMIN AND MINERAL SUPPLEMENT

(75) Inventors: Kenneth H. Cooper, Dallas, TX (US); Ishwarlal Jialal, Davis, CA (US); Scott Montgomery Grundy, Dallas, TX (US); Walter Churchill Willett, Cambridge, MA (US); Jacob Selhub, Brookline, MA (US)

(73) Assignee: Cooper Concepts, Inc., Dallas, TX (US)

( * ) Notice: Subject to any disclaimer, the term of this patent is extended or adjusted under 35 U.S.C. 154(b) by 309 days.

This patent is subject to a terminal disclaimer.

(21) Appl. No.: 10/279,708
(22) Filed: Oct. 25, 2002
(65) Prior Publication Data

US 2004/0082536 A1 Apr. 29, 2004

(51) Int. Cl.$^7$ .............................. A61K 9/28; A61K 9/48; A61K 9/20; A61K 9/14; A61K 9/26
(52) U.S. Cl. ...................... 424/441; 424/400; 424/451; 424/464; 424/468; 424/470; 424/489; 424/499; 424/502
(58) Field of Search .................................. 424/441, 400, 424/451, 464, 468, 470, 489, 499, 502

(56) References Cited

U.S. PATENT DOCUMENTS 6,299,896 B1 * 10/2001 Cooper et al. .............. 424/441

OTHER PUBLICATIONS

Killinger, Z; Payer, J Jr.; Sladekova, K; Kratochilova, M; Ondrejka, P.; Vnitrni Lekarstvi [Vnitr Lek] Aug. 1999; 45 (8), pp. 473–475.*
Francesco Nappo, MD, Ph.D. et al, "Impairment of Endothelial Functions by Acute Hyperhomocysteinemia and Reversal by Antioxidant Vitamins" American Medical Association, JAMA, vol. 281, No. 22, pp. 2113–2118. (Jun. 9, 1999).
L. Riddell, Alexandra Chisholm Sheila Williams, and Jim Mann, "Dietary Strategies for Lowering Homocysteine Concentrations $^{1-3}$",Am J. Clinical Nutrition 2000, 71:pps. 1448–1458; (Nov. 11, 1999).
George N. Welch, MD., Joseph Loscalzo, MD., Ph.D, "Homocysteine and Atherotherombosis" The New England Journal of Medicine, pps. 1042–1050, (Apr. 9, 1998).
Jayne V. Woodside, et al., Effect of B–group Vitamins and Antioxidant Vitamins on Hyperhomocysteinemia: A Double–blind, Randomized, Factorial–design, controlled trial $^{1-3}$, Am. Journal of Clinical Nutrition; 67, pp. 858–866, (1998).
Sridevi Devaraj and Ishwarlal Jialal, "Alpha–Tocopherol Decreases Interleukin–1β Release From Activated Human Monocytes by Inhibition of 5–Lipoxygenase", Center for Human Nutrition (S.D., I.I.) and Departments of Pathology (S.D., I.J.) and Internal Medicine (I.J.) University of Texas, Southwestern Medical Center, Dallas, TX. pps. 1125–1133, (Oct. 28, 1998).

Ishwarlal Jialal, Cindy J. Fuller and Beverley A. Huet, "The Effect of Alpha–Tocopherol Supplementation on LDL Oxidation: A Dose–Response Study", American Heart Association, Inc., Center for Human Nutrition, UT Southwestern Medical Center, pps. 190–198, (1995).
Olli P. Heinonen, et al., Prostate Cancer and Supplementation with Alpha–Tocopherol and β–Carotene: Incidence and Mortality in a Controlled Trial; Journal of the National Cancer Institute, vol. 90., No. 6, pps. 440–446, (Mar. 18, 1998).
Paul F. Jacques, et al., "Long–Term Vitamin C Supplement Use and Prevalence of Early Age–Related Lens Opacities$^{1-4}$", American Journal of Clinical Nutrition, 66:pp. 911–916, (1997).
Giuseppe Paolisso, et al, "Pharmacologic Doses of Vitamin E Improve Insulin Action in Healthy Subjects and Non–Insulin–Dependent Diabetic Patients $^{1,2}$"; American Journal of Clinical Nutrition; 57:pps. 650–666, (1993).
Gary D. Plotnick, MD, Mary C. Corretti, AND Robert A. Vogel,MD, "Effect of Antioxidant Vitamins on the Transient Impairment of Endothelium–Dependent Brachial Artery Vasoactivity Following a Single High–Fat Meal", JAMA, vol. 278, No. 20 pps. 1682–1688, (Nov. 26, 1997).
Marco N. Diaz et al, "Antioxidants and Atherosclerotic Heart Disease", The New England Journal of Medicine, pps. 408–416, (Aug. 7, 1997).
Timothy E. McAlindon, et al., "Do Antioxidant Micronutrients Protect Against The Development and Progression of Knee Osteroarthritis", Arthritis & rheumatisum vol. 39, No. 4, pps. 648–656, (Apr. 1996).
Bernadette Eberlein–Konig, MD, Marianne Placzek, MD, and Bernhard Przybilla, MD, "Protective Effect Against Sunburn of Combined Systemic Ascorbic Acid (Vitamin C) and d–Alpha–Tocopherol (vitamin E)", J. Am Acad Dermatol, 38: pps. 45–48, (1998).
Johanna M. Seddon, et al., "Dietary Carotenoids, Vitamins A, C, and E, and Advanced Age–Related Macular Degeneration", JAMA,vol. 272, No. 18, pps. 1413–1420, (Nov. 9, 1994).

(Continued)

Primary Examiner—James O. Wilson
Assistant Examiner—Paul V. Ward
(74) Attorney, Agent, or Firm—Tucker Ellis & West LLP

(57) ABSTRACT

This invention is directed to a multi-vitamin and mineral supplement tailored to men and post-menopausal women, pre-menopausal women, and athletes which supplies the right amount of the right micronutrients at the right time to assure adequate intake of micronutrients needed for disease prevention and protection against nutritional losses and deficiencies due to lifestyle factors and common inadequate dietary patterns. The multi-vitamin and mineral supplement is comprised of vitamin A, vitamin C, vitamin D, vitamin E, vitamin K, vitamin B1, vitamin B2, niacinamide, vitamin B6, vitamin B12, biotin, pantothenic acid, iron, iodine, magnesium, zinc, selenium, copper, chromium, potassium, choline, lycopene, and co-enzyme Q-10.

39 Claims, No Drawings

OTHER PUBLICATIONS

Nigel G. Stephens, et al., "Randomized Controlled Trial of Vitamin E in Patients with Coronary Disease: Cambridge Heart Antioxidant Study (CHAOS)",The Lancet, vol. 347, pps. 781–786, (Mar. 23, 1996).

Meir J. Stamper, MD., et al., "Vitamin E Consumption and the risk of coronary Disease in Women", the New England Journal of Medicine, vol. 328, No. 20, pps, 1444–1449, (May 20, 1993).

Eric B. Rimm, Sc.D., et al, "Vitamin E Consumption and the risk of Coronary Heart Disease in Men", The New England Jour5nal of Medicine, vol. 328, No. 20, pps. 1450–1456, (May 20, 1993).

Andreas Hartmann, et al., "Vitamin E. Prevents Exercise–Induced DNA Damage", Mutation Research 346, pps. 195–202, (1995).

Ranjit Kumar Chandra, "Graying of the Immune System: Can Nutrient Supplements Improve Immunity in the Elderly", JAMA, vol. 277, No. 17,.pps. 1398–1399, (May 7, 1997).

Meir J. Stampfer, MD, et al., "A Prospective Study of Plasma Homocyst(e)ine and Risk of Myocardial Infarction in US Physicians", JAMA vol., 268, No. 7, pps. 877–881, (Aug. 19, 1992).

Jacob Selhub, Ph.D., et al., "Association Between Plasma Homocysteine Concentrations and Extracranial Carotid–Artery Stenosis" The New England Journal of Medicine, pps. 286, (Feb. 2, 1995).

Hans J. Naurath, et al., "Effects of Vitamin B12, Folate, and Vitamin B6 Supplements in Elderly people with Normal Serum Vitamin Concentrations", The Lancet, vol., 346, pps. 85–89, (Jul. 8, 1995).

Egil Arnesen, et al., Serum total Homocysteine and Coronary Heart Disease, International Journal of Epidemiology, vol. 24, No. 4, pps. 704–709, (1995).

Carol J. Boushey, PhD, et al., "A Quantitative Assessment of Plasma Homocysteine as a Risk Factor for Vascular Disease", JAMA, vol. 274, No. 13, pps. 1049–1057, (Oct. 4, 1995).

Ottar Nygard, MD, et al., "Total Plasma Homocysteine and Cardiovascular Risk Profile: The Hordaland Homocysteine Study", JAMA, vol. 274, No. 19, pps. 1526–1533, (Nov. 15, 1995).

Nicholas J. Wald, DSc, et al., "Homocysteine and Ischemic Heart Disease", Arch Intern Med., vol. 158, pps. 862–867, (Apr. 27, 1998).

Manuel r. Malinow, et al., Reduction of Plama Homocyst(e)ine Levels By breakfast Cereal Fortified with Folic Acid in Patients With Coronary Heart Disease, The New England Journal of Medicine, vol. 338, No. 15, pps. 1009–1015, (Apr. 9, 1998).

Simin Nikbin Meydani, et al., "Vitamin E Supplementation and In Vivo Immune Response in Healthy Elderly Subjects", JAMA, vol. 277, No. 17, pps. 1380–1386, (May 7, 1997).

Ian M. Graham, et al., "Plasma Homocysteine as a Risk Factor for Vascular Disease: The European Concerted Action Project", JAMA, vol. 277, No. 22, pps. 1775–1781, (Jun. 11, 1997).

Eric B. Rimm, et al., "Folate and Vitamin $B_6$ From Diet and Supplements in Relation to Risk of Coronary Heart Disease Among Women", JAMA, vol. 279, No. 5, pps. 359–364, (Feb. 4, 1998).

Dienneke ZB van Asselt, et al., Role fo Colbalamin Intake and Atrophic Gastritis in Mild Cobalamin Deficiency in Older Dutch Subjects [1–3], Am. Journal Clinical Nutrition;68: pps. 328–334, (1998).

Katherine L. Tucker, et al., "Folic Acid Fortification of the Food Supply", JAMA, vol. 276, No. 23, pps. 1879–714, (Dec. 18, 1996).

Tomoko Shimakawa, et al., "Vitamin Intake: A Possible Determinant of Plasma Homocyst(e)ine Among Middle–Aged Adults", AEP, vol. 7, No. 4., pps. 285–293, (May 1997).

Gilbert S. Omenn, et al., "Preventing Coronary Heart Disease B Vitamins and Homocysteine", American Heart Association, Inc., pps. 421–424, (1998).

Ottar Nygard, et al., " Plasma Homocysteine Levels and Mortality in Patients with Coronary Artery Disease", The New England Journal of Medicine, vol. 337, No. 4, pps. 230–236, (Jul. 24, 1997).

Edward Giovannucci, et al., "Multivitamin Use, Folate, and Colon Cancer in Women in the Nurses' Health Study" Annals of Internal Medicine, vol. 129, No. 7, pps. 517–524, (Oct. 1, 1998).

Anja Bronstrup, et al., Effects of Folic Acid and combinations of Folic Acid and Vitamin B–12 on Plasma Homocysteine Concentrations in Healthy, Young Women [1,2], Am. Journal Clinical Nutrition, vol. 68, pps.1104–1110, (1998).

Larry C. Clark, et al., "Effects of Selenium Supplementation for Cancer Prevention in Patients With Carcinoma of the Skin: A Randomized Controlled Trial", JAMA, vol. 276, No. 24, pps. 1957–1963, (Dec. 25, 1996).

Melissa K. Thomas, et al., "Hypovitaminosis D in Medical inpatients", The New England Journal of Medicine, vol. 338, No. 12, pps. 777–783, (Mar. 19, 1998).

Mary Sano, et al., "A Controlled Trial of Selegiline, Alpha–Tocopherol, or Both as Treatment for Alzheimer's Disease", The New England Journal of Medicine, vol. 336, No. 17, pps. 1219–1222, (Apr. 24, 1997).

C. Douillet, et al., "Effect of Selenium and Vitamin E. Supplements on Tissue Lipids, peroxides, and Fatty Acid Distribution in Experimental Diabetes", Lipids, vol. 33, No. 4, pps. 393–99, (1998).

Killian Robinson, et al., "Low Circulating Folate and Vitamin $B_6$ Concentrations risk Factors for Stroke, peripheral Vascular Disease, and Coronary Artery Disease", American Heart Association, Inc., pps. 437–443, (1998).

L.C. Clark' et al., "decreased Incidence of Prostate Cancer with Selenium Supplementation: Results of a Double–Blind Cancer Prevention Trial", British Journal of Urology, vol. 81, pps. 730–734, (Jan. 12, 1998).

R. Aejmelaeus, et al., "Ubiquinol–10 and Total Peroxyl Radical Trapping Capacity of LDL Lipoproteins During Aging: The Effects of Q–10 Supplementation", Molec. Aspects Med., vol. 18, pps s113–s120, (1997).

Knud Lockwood, et al., "Partial and Complete Regression of Breast Cancer in Patients in Relation to Dosage of Coenzynme $Q_{10}$", Biochemical and Biophysical Research Communications, vol. 199, No. 3, pps. 1504–1508, (Mar. 30, 1994).

Francene M. Steinberg, et al., "Antioxidant Vitamin Supplementation and Lipid Peroxidation in Smokers[1–3]", Am J. Clin. Nutr., vol. 68, ps. 319–327, (1998).

Thomas Heitzer, et al., "Antioxidant Vitamin C Improves Endothelial Dysfunction in Chronic Smokers", Brief Rapid Communications, pps. 6–9, (1996).

Sanjiv Agarwal, et al., "Tomato Lycopene and Low Density lipoprotein Oxidation: A Human Dietary Intervention Study", Lipids, vol. 33, No. 10, pps. 981–983, (1998).

Joel A. Simon, et al., "Serum Ascorbic Acid and Other Correlates of Gallbladder Disease Among US Adults", American Journal of public Health, vol. 88, No. 8, ppsg. 1208–1212, (Aug. 1998).

Aaron R. Folsom, et al., Prospective Study of Coronary Heart Disease Incidence in relation to Fasting Total homocysteine, related Genetic Polymorphisms, and B Vitamins: The Atherosclerosis Risk in Communities (ARIC) Study, Clinical Investigation and Reports, vol. 98, pps. 204–210, (1998).

Joel A. Simon, et al., "Ascorbic Acid Supplement Use and the Prevalence of gallbladder Disease", J. Clin Epidemiol, vol. 51, No. 3, pps. 257–265, (1998).

Brigitte M. Winklhofer–Roob, et al., "Impaired resistance to oxidation of Low Density Lipoprotein in Cystic Fibrosis: Improvement During Vitamin E Supplementation", Free Radical Biology & Medicine, vol. 19, No. 6, pps. 725–733, (1995).

L. John Hoffer, "Nutritional Supplements and Health", Annals RCPSE, vol. 29, No. 1, pps. 11–16, (Feb. 1996).

"Environmental Nutrition" vol. 17, No. 10., pps. 3–4, (Oct. 1994).

Pauline Mendola, et al., "Dietary Correlates of Fat Intake", Nutrition and Cancer, vol. 23, No. 2, pps. 161–169, (1995).

Ralph L. Sacco, et al., "Homocysteine as A Risk Factor for Ischemic Stroke: An Epidemiological Story", Neuroepidemiology, vol. 17, pps. 167–173, (1998).

Nanci Hellmich, "Fighting Cancer: Diet and Exercise", USA Today, Section: Life, p. 1D, (Oct. 1, 1997).

Simin Nikbin Meydani, et al., "Vitamin E Supplementation and In Vivo Immune Response in Healthy Elderly Subjects", Journal of the American Medical Association, vol. 277, No. 17, pps. 1380–1386, (May 7, 1997).

Ranjit Kumar Chandra, "Commentary—Graying of the Immune System, Can Nutrient Supplements Improve Immunity in the Elderly?", The Journal of the American Medical Association, vol. 277, No. 17, pps. 1398–1399, Abstract, (May 7, 1997).

Melissa K. Thomas, et al., Hypovitaminosis D in Medical Inpatients, The New England Journal of Medicine, vol. 338, No. 12, pps. 777–783, Abstract, (Mar. 19, 1998).

Michael F. Holick, "Vitamin D and Bond Health" Symposium: Nutritional Advances in Human Bone Metabolism, pps. 1159S–1164S, (1996).

B.W. Ogunkolade, et al., "Expression of 25–Hydroxyvitamin D–1–Alpha–Hydroxylase mRNA in Individuals with Colorectal Cancer", The Lancet, vol. 359, pps. 1831–1832, (May 25, 2002).

B.W. Ogunkolade, et al., "Expression of 25–Hydroxyvitamin D–1–Alpha–Hydroxylase mRNA in Individuals with Colorectal Cancer", National Library of Medicine, Abstract, (Aug. 30, 2002).

Robert H. Fletcher, et al., "Vitamins for Chronic Disease Prevention in Adults", Journal of the American Medical Association, vol. 287, No. 23, pps. 3127–3129, (Jun. 19, 2002).

Robert D. Utiger, "The Need for More Vitamin D", The New England Journal of Medicine, pps. 828–829, (Mar. 19, 1998).

P.R. Holt, et al., "Colonic Epithelial Cell Proliferation Decreases with Increasing Levels of Serum 25–Hydroxy Vitamin D", Cancer Epidemiol Biomarkers, , (May 11, 2002).

Michael F. Holick, "McCollum Award Lecture, 1994: Vitamin D—New Horizons for the 21st Century", American Journal for Clinical Nutrition, vol. 60, pps. 619–630, (1994).

Bess Dawson–Hughes, "Effect of Calcium and Vitamin D Supplementation on Bone Density in Men and Women 65 Years of Age or Older", The New England Journal of Medicine, pps. 670–676, (Sep. 4, 1997).

Paul F. Jacques, et al., "Plasma 25–Hydroxyvitamin D and Its Determinants in an Elderly Popultion Sample", American Journal of Clinical Nutrition, vol. 66, pp. 929–936, (1997).

Marie C. Chapuy, et al., "Vitamin $D_3$ and Calcium to Prevent Hip Fractures in Elderly Women", The New England Journal of Medicine, vol. 327, No. 23, pps. 1637–1642, (Dec. 3, 1992).

A.R. Webb, et al., "Influence of Season and Latitude on the Cutaneous Synthesis of Vitamin $D_3$: Exposure to winter Sunlight in Boston and Edmonton Will Not Promote Vitamin $D_3$ Synthesis in Human Skin", Journal of Clinical Endocrinology and Metabolism, vol. 67, No. 2, pps. 373–378, (1988).

U. Peters, et al., "Vitamin D, Calcium, and Vitamin D. Receptor Polymorphism in Colorectal Adenomas", Division of Cancer Epidemiology and Genetics, National Cancer Institute, Bethesda, Maryland 20892, National Library of Medicine, Abstract, (Dec. 10, 2001).

* cited by examiner

MULTI-VITAMIN AND MINERAL SUPPLEMENT

BACKGROUND OF THE INVENTION

This invention is directed to multi-vitamin and mineral supplements. In particular, this invention is directed to multi-vitamin and mineral supplements for improving health by insuring adequate intake of micronutrients needed for disease prevention and protection against nutritional losses and deficiencies due to such factors as lifestyle patterns and common inadequate dietary patterns. More particularly, this invention is directed to multi-vitamin and mineral supplements for ameliorating vitamin D deficiency, maintaining good bone health, and preventing colorectal cancer.

Vitamin and mineral preparations are commonly administered to treat specific medical conditions or as general nutritional supplements. Micronutrients are elements or compounds which are present in foods in small or trace amounts and includes vitamins, minerals, or other elements, and compounds found in foods for which a Recommended Daily Allowance (RDA) has not yet been determined. The macronutrients consist of carbohydrates, fats, and proteins which supply nutrients and calories. Some elements such as calcium, sodium, potassium, chloride, and phosphorus are consumed in relatively large amounts, while many such as iron, iodine, and zinc are consumed in small amounts. Vitamins, such as B12 and folic acid, and the minerals cooper, selenium, and chromium are consumed in very small or trace amounts. In as much as the human body does not synthesize many compounds which are essential to the human body, these specific vitamins and minerals can be obtained from only two sources: food and supplements. The primary source of all nutrients is food. However, the majority of people do not meet the RDA of the foods containing these essential compounds and elements. Thus, vitamin and mineral supplementation has become a recognized method of meeting accepted medical and health standards.

An international panel of diet and cancer experts announced in London on Sep. 30, 1997, that as many as 30 to 40 percent of all cancer cases worldwide—3 to 4 million a year-could be avoided if people ate a healthy diet and got enough exercise. *USA Today*, Oct. 1, 1997. However, for some nutrients, the amounts proposed as being healthy apparently cannot be provided by a reasonable quantity and variety of natural foods. Thus, nutrient supplements may be important for health promotion and prevention of chronic diseases. *Journal of the American Medical Association*, May 7, 1997.

Recent studies have illustrated the important physiological roles played by vitamins and minerals and established a correlation between deficiencies or excesses of these nutrients and the etiologies of certain disease states in humans. Suboptimal levels of a vitamin are defined as those associated with abnormalities of metabolism that can be corrected by supplementation with that vitamin. Studies have shown that there is a high prevalence of suboptimal vitamin levels implies that the usual U.S. diet provides an insufficient amount of these vitamins. For example, although vitamin D is added to milk, many people do not consume enough dairy products to get a sufficient amount of vitamin D.

Vitamin D is an essential precursor of 1,25-dihydroxyvitamin D, the steroid hormone required for bone development and growth in children maintenance of bone in adults, and the prevention of osteoporosis and fractures in the elderly. Studies have found low values of vitamin D in 46 percent of the patients taking multivitamins, many of which contain 400 I.U. of vitamin D, which is the RDA. *The New England Journal of Medicine*, Mar. 19, 1998. Studies have also shown that an increase in calcium intake of 800 to 1000 mg/d with supplementation of greater than 400 to 800 I.U. of vitamin D daily will decrease the risk of vertebral and nonvertebral fractures and increase bone mineral density. *Symposium: Nutritional Advances in Human Bone Metabolism*, American Institute of Nutrition, 1996.

In addition, evidence has suggested that vitamin D has potential role in colon cancer prevention. Studies have shown that vitamin D prevents profileration, promotes differentiation, and induces apoptosis of colon cells, and that reduced intake or insufficiency of vitamin D are associated with increased risk of colorectal cancer. *Expression of 25-hydroxyvitamin D-1-alpha-hydroxylase mRNA in individuals with colorectal cancer*, May 25, 2002; *Vitamin D, calcium, and vitamin D receptor polymorphism in colorectal adenomas*, Dec. 10, 2001.

There exists a need for a nutritional supplement which supplies the right amount of the right micronutrients at the right time to assure adequate intake of micronutrients, particularly vitamin D, needed for disease prevention and protection against nutritional losses and deficiencies due to lifestyle factors and common inadequate dietary patterns.

SUMMARY OF THE INVENTION

In accordance with the present invention, there is provided a multi-vitamin and mineral supplement which supplies the right amount of the right micronutrients at the right time to assure adequate intake of micronutrients needed for disease prevention and protection against nutritional losses and deficiencies due to lifestyle factors and common inadequate dietary patterns.

Further, in accordance with the present invention, there is provided a new and improved multi-vitamin and mineral supplement which can be used for providing the necessary nutrients to allow the users of such supplement to maintain their present health and positively influence their future health.

Still further, in accordance with the present invention, there is provided a multi-vitamin and mineral supplement which provides an adequate amount of vitamin D for ameliorating vitamin D deficiency, maintaining good bone health, and preventing colorectal cancer.

Still further in accordance with the present invention, there is provided a multi-vitamin and mineral supplement for administration to humans comprising:

from about 5000 I.U. to about 10,000 I.U. of vitamin A;
from about 1000 mg to about 2000 mg of vitamin C;
about 800 I.U. of vitamin D;
from about 400 I.U. to about 1200 I.U. of vitamin E;
about 25 mcg of vitamin K;
about 3 mg of vitamin B1;
about 10 mg of vitamin B2;
about 20 mg of B3;
from about 25 mg to about 50 mg of vitamin B6;
about 800 mcg of folic acid;
about 400 mcg of vitamin B12;
about 300 mcg of biotin;
about 10 mg of pantothenic acid;
up to about 18 mg of iron dosed in the form of a pharmaceutically acceptable iron compound;

about 150 mcg of iodine dosed in the form of a pharmaceutically acceptable iodine compound;

about 400 mg of magnesium dosed in the form of a pharmaceutically acceptable magnesium compound;

about 15 mg of zinc dosed in the form of a pharmaceutically acceptable zinc compound;

from about 100 mcg to about 200 mcg of selenium;

about 2 mg of copper dosed in the form of a pharmaceutically acceptable copper compound;

from about 65 mcg to about 100 mcg of chromium dosed in the form of a pharmaceutically acceptable chromium compound;

about 400 mg of potassium dosed in the form of a pharmaceutically acceptable potassium compound;

about 500 mg of choline dosed in the form of a pharmaceutically acceptable choline compound;

from about 5 mg to about 10 mg of lycopene; and from about 50 mg to about 100 mg co-enzyme Q-10 dosed in the form of a pharmaceutically acceptable co-enzyme Q-10 compound.

An advantage of the present invention is that the multi-vitamin and mineral supplement supplies the right amount of the right micronutrients at the right time to assure adequate intake of micronutrients needed for disease prevention and protection against nutritional losses and deficiencies due to lifestyle factors and common inadequate dietary patterns.

Another advantage of the present invention is that the multi-vitamin and mineral supplement provides the necessary nutrients to allow the users of such supplement to maintain their present health and positively influence their future health.

Another advantage of the present invention is that the multi-vitamin and mineral supplement provides an adequate amount of vitamin D for ameliorating vitamin D deficiency, maintaining good bone health, and preventing colorectal cancer.

These and other advantages and benefits of the invention will be apparent to those skilled in the art upon reading and understanding of the following detailed description.

DETAILED DESCRIPTION OF THE PREFERRED EMBODIMENT

This invention is directed to a multi-vitamin and mineral supplement which supplies the right amount of the right micronutrients at the right time to assure adequate intake of micronutrients needed for disease prevention and protection against nutritional losses and deficiencies due to lifestyle factors and common inadequate dietary patterns. The multi-vitamin and mineral supplement is comprised of vitamin A; vitamin C; vitamin D; vitamin E; vitamin K; vitamin B1; vitamin B2; vitamin B3; vitamin B6; folic acid; vitamin B12; biotin; pantothenic acid; iron; iodine; magnesium; zinc; selenium; copper; chromium; potassium; choline; lycopene; and co-enzyme Q-10.

All amounts specified in the application are based on milligrams unless otherwise indicated. The term "I.U." represents International Units.

The multi-vitamin and mineral supplement is comprised of vitamin A. Vitamin A prevents night blindness and other eye disorders, keeps skin moist and elastic, maintains healthy hair, skin, and gums, reduces the risk of breast cancer, helps alleviate mastodynia, reduces the risk of lung cancer, maintains cell structure and integrity, works as antioxidant to prevent cell aging, helps prevent infection, and negates skin wrinkling and the effects of sun damage.

Vitamin A is a fat soluble vitamin. The term vitamin A is used to include retinol and other chemically similar compounds referred to as retanoids. Beta-carotene and other carotenoids are provitamins and are only turned into retinol as the body requires. Preferably, in the multi-vitamin and mineral supplement, vitamin A is provided in the form of beta-carotene and other mixed carotenoids. Preferably, the mixed carotenoids are lutein and zeaxanthine. Lutein and zeaxanthine have been found to decrease the risk and even reverse the development of macular degeneration, the leading cause of blindness in those over the age of 65.

In one embodiment, the multi-vitamin and mineral supplement is comprised of about 5000 I.U. of vitamin A and about 14 mcg of lutein and zeaxanthine. More preferably, the multi-vitamin and mineral supplement is comprised of about 5000 I.U. of vitamin A in the form of natural mixed beta-carotene and about 14 mcg of lutein and zeaxanthine.

For pre-menopausal women, post-menopausal women, and men, the multi-vitamin and mineral supplement is preferably comprised of about 5000 I.U. of vitamin A and about 6000 mcg of lutein and zeaxanthine. More preferably, the multi-vitamin and mineral supplement is comprised of about 5000 I.U. of vitamin A in the form of natural mixed beta-carotene and about 6000 mcg of lutein and zeaxanthine. The amount of lutein and zeaxanthine present in the multi-vitamin and mineral supplement must be sufficient to ensure that one's intake of these carotenoids is adequate to achieve the benefits associated with these carotenoids.

For athletes, the multi-vitamin and mineral supplement is preferably comprised of about 10,000 I.U of vitamin A and about 6000 mcg of lutein and zeaxantine. More preferably, the multi-vitamin and mineral supplement is comprised of about 10,000 I.U. of vitamin A in the form of natural mixed beta-carotene and about 6000 mcg of lutein and zeaxanthine. The higher level of vitamin A present in this formulation is required to fight the high level of free-radicals produced by athletes. The body's need for oxygen during exercise produces free radicals, which can oxidize the fats in muscle cell membranes in a process known as "lipid preoxidation" and which make the cells more susceptible to aging and other damage.

Vitamin C, also known as ascorbic acid, is necessary for the synthesis of collagen and is used as an antioxidant. Vitamin C fights infection, reduces inflammation, heals wounds, reduces the risk of heart disease, lowers cholesterol, reduces the risk of lung, stomach, and esophageal cancers, reduces cervical epithelial abnormalities, inhibits N-nitrosamine, and reduces the severity of colds. In one embodiment, the multi-vitamin and mineral supplement is comprised of about 1000 mg of vitamin C.

For pre-menopausal women, post menopausal women, and men, the multi-vitamin and mineral supplement is preferably comprised of about 1000 mg of vitamin C. For athletes, the multi-vitamin and mineral supplement is preferably comprised of about 2000 mg of vitamin C. The higher level of vitamin C is required to fight the high level of free-radicals produced by athletes and helps to revive vitamin E.

Vitamin D is also an essential vitamin that is included in the multi-vitamin and mineral supplement of the present invention. Vitamin D assists in the mineralization and calcification of bone, prevents rickets in children, prevents osteomalacia in adults, preserves bone and tooth growth, lowers blood pressure and helps prevent colorectal cancer. Vitamin D is fat soluble. Preferably, the multi-vitamin and mineral supplement is comprised of about 800 I.U. of vitamin D.

Vitamin E is needed for the maintenance of cell membranes and for neurological health. Vitamin E relieves hot flashes, relieves mastodynia, helps in fighting fibrocystic breast disease, reduces mammary tumors, reduces the risk of lung cancer, and reduces the risk of heart disease. Vitamin E is the generic term for a group of related substances which include alpha-tocopherol, beta-tocopherol, gamma-tocopherol, and delta-tocopherol. In addition, each of these four compounds have a "d" form, which is the natural form, and a "dl" form which is the synthetic form. Preferably, in the multi-vitamin and mineral supplement, vitamin E is provided in the form of d-alpha tocopherol succinate.

For pre-menopausal women, post-menopausal women, and men, the multi-vitamin and mineral supplement is preferably comprised of about 800 I.U. of vitamin E. More preferably, the multi-vitamin and mineral supplement is comprised of about 800 I.U. of vitamin E in the form of d-alpha tocopherol succinate. Research has shown that 400 I.U. of vitamin E is the minimum dosage needed to significantly decrease susceptibility of LDL cholesterol to oxidation. Patients with coronary atherosclerosis which were taking 400 or 800 I.U. of vitamin E daily had a statistically significant reduction in the incidence of non-fatal myocardial infarction. Therefore, the amount of vitamin E present in the multi-vitamin and mineral supplement must be sufficient to ensure that one's intake of vitamin E is adequate to achieve the benefits associated with vitamin E.

For athletes, the multi-vitamin and mineral supplement is preferably comprised of about 1200 I.U. of vitamin E. More preferably, the multi-vitamin and mineral supplement is comprised of about 1200 I.U. of vitamin E in the form of d-alpha tocopherol succinate. The higher level of vitamin E present in this formulation is required to fight the high level of free-radicals produced by athletes.

The multi-vitamin and mineral supplement includes vitamin K. Vitamin K is an active blood clotting agent and assists in bone formation. Preferably, the multi-vitamin and mineral supplement is comprised of about 25 mcg of vitamin K.

The multi-vitamin and mineral supplement is comprised of most of the B complex of vitamins. The B vitamins are water-soluble. The B vitamins included in the multi-vitamin and mineral supplement are thiamin (vitamin B1), riboflavin (vitamin B2), niacin (vitamin B3), pantothenic acid (vitamin B5), pyridoxine (vitamin B6), biotin, folic acid, the cobalamins (vitamin B12), and choline.

Vitamin B1 or thiamin helps keep collagen-rich connective and mucous membranes healthy, helps to maintain smooth muscles, helps in the formation of blood cells, and is necessary for proper nervous system function. Preferably, the multi-vitamin and mineral supplement is comprised of about 3 mg of vitamin B1.

Vitamin B2 or riboflavin is necessary for healthy hair, nails, and mucous membranes and is involved in red blood cell formation, antibody production, and overall growth. Preferably, the multi-vitamin and mineral supplement of the present invention is comprised of about 10 mg of vitamin B2.

Vitamin B3 or niacin helps in the production of most of the sex hormones, dilates blood vessels, lowers cholesterol, and helps maintain blood circulation. Niacin is the generic name for a group of compounds which exhibit niacin activity, and includes niacinamide and nicotinic acid. Preferably, in the multi-vitamin and mineral supplement, vitamin B3 is provided as niacinamide. Preferably, the multi-vitamin and mineral supplement is comprised of about 20 mg of vitamin B3. More preferably, the multi-vitamin and mineral supplement is comprised of about 20 mg of vitamin B3 in the form of niacinamide.

Vitamin B6 or pyridoxine is involved in the production of ribonucleic acid (RNA) and deoxyribonucleic acid (DNA) and many other reactions in the body. Pyridoxine refers to and includes three different compounds: pyridoxine, pyridoxamine, and pyridoxal. Preferably, in the multi-vitamin and mineral supplement, vitamin B6 is in the form of pyridoxine hydrochloride.

Preferably, the multi-vitamin and mineral supplement is comprised of about 25 mg of vitamin B6. More preferably, the multi-vitamin and mineral supplement is comprised of about 25 mg of vitamin B6 in the form of pyridoxine hydrochloride. Vitamin B6, when combined with folic acid and vitamin B12, has been found to decrease homocysteine levels. Such decreases in homocysteine levels have been found with about 25 mg to about 50 mg of vitamin B6.

Folic acid is essential in the production of red blood cells, the production of hormones, and the synthesis of DNA. Preferably, the multi-vitamin and mineral supplement is comprised of about 800 mcg of folic acid.

Vitamin B12 or the cobalamins is necessary for overall metabolism, the function of the nervous system, metabolism of folic acid, and the production of red blood cells. There are at least three active forms of cobalamin: cyanocobalamin, hydroxocobalamin, and nitrocobalamin. Preferably, in the multi-vitamin and mineral supplement of the present invention, vitamin B12 is provided in the form of cyanocobalamin. Preferably, the multi-vitamin and mineral supplement is comprised of about 400 mcg of vitamin B12. More preferably, the multi-vitamin and mineral supplement is comprised of about 400 mcg of vitamin B12 in the form of cyanocobalamin.

Biotin is necessary for the metabolism of carbohydrates, proteins, and fats and is needed for healthy skin and hair. Preferably, in the multi-vitamin and mineral supplement, biotin is provided in the form of d-biotin. Preferably, the multi-vitamin and mineral supplement is comprised of about 300 mcg of biotin. More preferably, the multi-vitamin and mineral supplement is comprised of about 300 mcg of biotin in the form of d-biotin.

Pantothenic acid is important for the production of adrenal gland hormones, increases overall energy, and helps convert food into energy. Preferably, in the multi-vitamin and mineral supplement, pantothenic acid is in the form of d-calcium pantothenate. Preferably, the multi-vitamin and mineral supplement is comprised of about 10 mg of pantothenic acid. More preferably, the multi-vitamin and mineral supplement is comprised of about 10 mg of pantothenic acid in the form of d-calcium pantothenate.

Choline is necessary for nervous system function and brain function. It is also important for gall bladder and liver function. Preferably, in the multi-vitamin and mineral supplement, choline is provided in the form choline bitartrate. Preferably, the multi-vitamin and mineral supplement is comprised of about 500 mg of choline. More preferably, the multi-vitamin and mineral supplement is comprised of about 500 mg of choline in the form of choline bitartrate.

Iron is used in the production of hemoglobin and myoglobin. In the multi-vitamin and mineral compound, the iron is dosed in the form of a pharmaceutically acceptable iron compound. As used herein, pharmaceutically acceptable is a component which is suitable for use in humans without undue side effects, such as irritation, toxicity, and allergic response. Useful pharmaceutically acceptable iron compounds include, but are not limited to, ferrous fumarate, ferrous sulfate, iron carbonyl, ferrous glucomate, ferrous chloride, ferrous lactate, ferrous tartrate, ferrous succinate, ferrous glutamate, ferrous citrate, ferrous pyrophosphate, ferrous cholinisocitrate, ferrous carbonate, iron-sugar-carboxylate complexes, and combinations thereof. Preferably, the pharmaceutically acceptable iron compound is iron carbonyl. Iron carbonyl is easier on the digestive tract than other forms of iron, such as ferrous fumerate. In addition, the Food and Drug Administration does not require a warning label on the toxicity to children for this form of iron as it is safe for children who accidentally ingest this form of iron.

For post-menopausal women and men, the multi-vitamin and mineral supplement is substantially free of iron. Research has shown that high stored levels of iron are associated with an increased risk of myocardial infarction. Post menopausal women and men do not need additional iron through supplements, unless otherwise recommended by a physician. In addition, a growing percentage of the population suffers from a disease known as hemochromatosis, an abnormally high level of iron in the blood. These people cannot take iron in supplement form.

For pre-menopausal women and athletes, the multi-vitamin and mineral compound is preferably, comprised of about 18 mg of iron dosed in a pharmaceutically acceptable iron compound. More preferably, the multi-vitamin and mineral supplement is comprised of about 18 mg of iron dosed in the form of iron carbonyl. Women in their child-bearing years need supplemental iron as deficiencies are common. Iron deficiencies are also common in athletes.

Iodine helps to metabolize fats, is necessary for proper thyroid function, and reduces fibrocystic breast conditions. In the multi-vitamin and mineral supplement of the present invention, iodine is dosed in the form of a pharmaceutically acceptable iodine compound. Useful pharmaceutically acceptable iodine compounds include, but are not limited to, potassium iodide, sodium iodide, and combinations thereof.

Preferably, the pharmaceutically acceptable iodine compound is potassium iodide. Preferably, the multi-vitamin and mineral supplement is comprised of about 150 mcg of iodine dosed in the form of a pharmaceutically acceptable iodine compound. More preferably, the multi-vitamin and mineral supplement is comprised of about 150 mg of iodine dosed in the form of potassium iodide.

Magnesium is used in bone formation and growth, prevents bone loss, relaxes coronary arteries, is used in managing pre-eclampsia, treating cardiac arrhythmias, and managing diabetes. In the multi-vitamin and mineral supplement, magnesium is dosed in the form of a pharmaceutically acceptable magnesium compound. Useful pharmaceutically acceptable magnesium compounds include, but are not limited to, magnesium stearate, magnesium carbonate, magnesium oxide, magnesium hydroxide, magnesium sulfate, and combinations thereof.

Preferably, the pharmaceutically acceptable magnesium compound is magnesium oxide. Preferably, the multi-vitamin and mineral supplement is comprised of about 400 mg of magnesium dosed in the form of a pharmaceutically acceptable magnesium compound. More preferably, the multi-vitamin and mineral supplement is comprised of about 400 mg of magnesium dosed in the form of magnesium oxide.

Zinc is required for proper formation of DNA and RNA and is needed for growth and sexual development of women. In the multi-vitamin and mineral supplement of the present invention, zinc is dosed in the form of a pharmaceutically acceptable zinc compound.

Pharmaceutically acceptable zinc compounds include, but are not limited to, zinc sulfate, zinc chloride, zinc oxide, and combinations thereof. Preferably, the pharmaceutically acceptable zinc compound is zinc oxide.

Preferably, the multi-vitamin and mineral supplement is comprised of about 15 mg of to zinc dosed in the form of a pharmaceutically acceptable zinc compound. More preferably, the multi-vitamin and mineral supplement is comprised of about 15 mg of zinc dosed in the form of zinc oxide.

Selenium reduces the risk of heart attacks and heart disease, reduces the risk of cancer, protects against metal poisoning, and is synergistic with vitamin E. Preferably, in the multi-vitamin and mineral supplement, selenium is obtained from rice bran chelate.

For pre-menopausal women, post-menopausal women, and men, the multi-vitamin and mineral supplement is preferably comprised of about 100 mcg of selenium. For athletes, the multi-vitamin and mineral supplement is preferably comprised of about 200 mcg of selenium.

The higher level of selenium is required to fight the high level of free-radicals produced by athletes and selenium works synergistically with vitamin E.

Copper helps keep blood vessels elastic, is needed for the formation of elastin and collagen, functions as an iron oxidizer, and is needed for the proper functioning of vitamin C. In the multi-vitamin and mineral supplement, copper is dosed in a pharmaceutically acceptable copper compound. Pharmaceutically acceptable copper compounds include, but are not limited to, cupric oxide, cupric sulfate, cupric gluconate, and combinations thereof. Preferably, the pharmaceutically acceptable copper compound is cupric gluconate.

Preferably, the multi-vitamin and mineral supplement is comprised of about 2 mg of copper dosed in the form of a pharmaceutically acceptable copper compound. More preferably, the multi-vitamin and mineral compound is comprised of about 2 mg of copper dosed in the form of cupric gluconate.

Chromium assists in the regulation of glucose metabolism, is used in the synthesis of fatty acids and cholesterol, assists in transporting proteins, lowers LDL blood levels, and raises high density lipoproteins blood levels. In the multi-vitamin and mineral supplement, chromium is dosed in a pharmaceutically acceptable chromium compound. Useful pharmaceutically acceptable chromium compounds include, but are not limited to, yeast-bound chromium, GTF chromium, niacin-bound chromium. Preferably, the pharmaceutically acceptable chromium compound is chromium amino acid chelate.

Preferably, the multi-vitamin and mineral supplement is comprised of about 100 mcg of chromium dosed in the form of a pharmaceutically acceptable chromium compound. More preferably, the multi-vitamin and mineral supplement is comprised of about 100 mcg of chromium dosed in the form of chromium amino acid chelate. Chromium is present in the multi-vitamin and mineral supplement at a level that meets the 100% daily value. Research has shown that the average person consumes less than 50 mcg of chromium a day.

Potassium is needed to regulate water balance, levels of acidity, blood pressure, and neuromuscular function. Potassium is also required for carbohydrate and protein metabolism. In the multi-vitamin and mineral supplement, potassium is dosed in the form of a pharmaceutically acceptable potassium compound. Useful pharmaceutically acceptable potassium compounds include, but are not limited to, potassium chloride, potassium glycerophosphate, potassium citrate, potassium gluconate, potassium phosphate, and combinations thereof. Preferably, the pharmaceutically acceptable potassium compound is potassium phosphate.

Preferably, the multi-vitamin and mineral supplement is comprised of about 400 mg of potassium dosed in the form of a pharmaceutically acceptable potassium compound. More preferably, the multi-vitamin and mineral supplement is comprised of about 400 mg of potassium dosed in the form of potassium phosphate.

Lycopene has been found to reduce the risk of cancer and has antioxidant capabilities. Lycopene is found primarily in tomatoes, red grapefruit, watermelon, and other sources, and is a carotenoid. Preferably, in the multi-vitamin and mineral supplement, the lycopene is obtained from tomatoes.

Preferably, the multi-vitamin and mineral supplement is comprised of about 10 mg of lycopene. Lycopene has been linked to lower rates of prostate cancer. Research has shown that four to seven servings of red tomato products per week can reduce deaths from prostate cancer by 20%. Therefore, the amount of lycopene present in the multi-vitamin and mineral supplement must be sufficient to ensure that one's intake of lycopene is adequate to achieve the benefits associated with lycopene.

Co-enzyme Q10, also known as ubiquinone, is an antioxidant which protects the body from radicals. Co-enzyme Q10 aids metabolic reactions, such as the complex process of transforming food into ATP, and helps people with congestive heart failure and angina. Co-enzyme Q10 is depleted in people taking lovastatin and pravastatin which are cholesterol lowering drugs.

Preferably, the multi-vitamin and mineral supplement is comprised of about 50 mg of co-enzyme Q10. Co-enzyme Q10 is very costly and the amount of co-enzyme Q10 present in the multi-vitamin and mineral supplement is sufficient to ensure that one's intake of co-enzyme Q10 is adequate to achieve the benefits associated with co-enzyme Q10.

The nutritional supplements of the present invention are suitably provided in any suitable dosage form known in the art. For example, the compositions are suitably incorporated into tablets, powders, granules, beads, chewable lozenges, capsules, liquids, or similar conventional dosage forms, using conventional equipment and techniques known in the art. Tablet dosage forms are preferred.

When preparing dosages forms incorporating the compositions of the present invention, the nutritional components are normally blended with conventional excipients such as binders, including gelatin, pregelatinzed starch, and the like; lubricants, such as hydrogenated vegetable oil, stearic acid and the like; diluents, such as lactose, mannose, and sucrose; disintegants, such as carboxymethyl cellulose and sodium starch glycolate; suspending agents, such as povidone, polyvinyl alcohol, and the like; absorbents, such as silicon dioxide; preservative, such as methylparaben, propylparaben, and sodium benzoate; surfactants, such as sodium lauryl sulfate, polysorbate 80, and the like; and colorants, such as F.D & C. dyes and the like.

For preparing the composition from the compounds described by this invention, inert, pharmaceutically acceptable carriers are used which are either solid or liquid form. Solid form preparations include powders, tablets, dispersible granules, capsules, and cachets. A solid carrier is suitably one or more substances which may also act as diluents, flavoring agents, solubilizers, lubricants, suspending agents, binders or tablet disintegrating agents. The solid carrier material also includes encapsulating material. In powders, the carrier is finely divided active compounds. In the tablet, the active compound is mixed with the carrier having the necessary binding properties in suitable proportions and compacted in the shape and size desired. Suitable solid carriers include, but are not limited, to magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term preparation is intended to include the formulation of the active compounds with encapsulating material as the carrier providing a capsule in which the active component (with or without other carriers) is surrounded by carrier, which is thus in association with it. Tablets, powders, cachets, and capsules may be used in a solid dosage form suitable for oral administration.

Liquid form preparations include solutions, suspensions, and emulsions. Aqueous solutions suitable for oral use are prepared by dissolving the active component in water or other suitable liquid and adding suitable colorants, flavors, stabilizing agents, and thickening agents as desired. Aqueous solutions suitable for oral use may also be made by dispersing the finely divided active component in water or other suitable liquid with viscous material, such as natural or synthetic gums, resins, methylcellulose, sodium carboxymethylcellulose, and other suspending agents known in the art.

Also included are solid form preparations which are intended to be converted, shortly before use, to liquid form preparations for either oral or parental administration. Such liquid forms include solutions, suspensions, and emulsions. These particular solid form preparations are provided in unit dose form and as such are used to provide a single liquid dosage unit. Alternatively, sufficient solid preparation may be provided so that the after conversion to liquid form, multiple individual liquid doses may be obtained by measuring predetermined volumes of the liquid form preparation as with a syringe, teaspoon, or other volumetric contained.

The solid and liquid forms may contain, in addition to the active material, flavorants, colorants, stabilizers, buffers, artificial and natural sweeteners, dispersants, thickeners, solubilizing agents, and the like. The liquid utilized for preparing the liquid form preparation is suitably water, isotonic water, ethanol, glycerin, propylene glycol, and the like, as well as combinations thereof. The liquid utilized will be chosen with regard to the route of administration.

Preferably, the preparations are unit dosage form. In such form, the preparation is subdivided into unit doses containing appropriate quantities of the active components. The unit dosage form can be a packaged preparation, such as packaged tablets or capsules. The unit dosage can be a capsule, cachet, or tablet itself or it can be the appropriate number of any of these in packaged form.

The quantity of active material in a unit dose of preparation is varied according to the particular application and potency of the active ingredients.

Determination of the proper dosage for a particular situation is within the skill of the art. For convenience, the total daily dosage may be divided and administered in portions during the day if desired. Controlled and uncontrolled release formulations are also included.

Although the products of the invention are preferably intended for administration to humans, it will be understood that the formulation may also be utilized in veterinary therapy for other animals.

While various embodiments of a multi-vitamin and mineral supplement have been disclosed, it should be understood that modifications and adaptations thereof will occur to one skilled in the art. Other features and aspects of this invention will be appreciated by those skilled in the art upon reading and comprehending this disclosure. Such features, aspects, and expected variations and modifications of the reported results and examples are clearly within the scope of the invention where the invention is limited solely by the scope of the following claims.

Having thus defined the invention, it is claimed:

1. A multi-vitamin and mineral supplement for administration to humans, the supplement comprising:
   from about 5000 I.U to about 10,000 I.U. of vitamin A;
   from about 1000 mg to about 2000 mg of vitamin C;
   about 800 I.U. of vitamin D;
   from about 800 I.U. to about 1200 I.U. of vitamin E;
   about 25 mcg of vitamin K;
   about 3 mg of vitamin B1;
   about 10 mg of vitamin B2;
   about 20 mg of vitamin B3;
   about 25 mg of vitamin B6;
   about 800 mcg of folic acid;
   about 400 mcg of vitamin B12;
   about 300 mcg of biotin;
   about 10 mg of pantothenic acid;
   up to about 18 mg of iron dosed in the form of a pharmaceutically acceptable iron compound;
   about 150 mcg of iodine dosed in the form of a pharmaceutically acceptable iodine compound;
   about 400 mg of magnesium dosed in the form of a pharmaceutically acceptable magnesium compound;
   about 15 mg of zinc dosed in the form of a pharmaceutically acceptable zinc compound;
   from about 100 mcg to 200 mcg of selenium;
   about 2 mg of copper dosed in the form of a pharmaceutically acceptable copper compound;
   about 100 mcg of chromium dosed in the form of a pharmaceutically acceptable chromium compound;
   about 400 mg of potassium dosed in the form of a pharmaceutically acceptable potassium compound;
   about 500 mg of choline dosed in the form of a pharmaceutically acceptable choline compound;
   about 10 mg of lycopene; and
   about 50 mg co-enzyme Q-10 dosed in the form of a pharmaceutically acceptable co-enzyme Q-10 compound.

2. The multi-vitamin and mineral supplement of claim 1 wherein the supplement is further comprised of 6000 mcg of lutein and zeaxanthine.

3. The multi-vitamin and mineral supplement of claim 1 wherein vitamin A is in the form of natural mixed beta carotene and carotenoids.

4. The multi-vitamin and mineral supplement of claim 1 wherein the multi-vitamin and mineral supplement is comprised of about 5000 I.U. of vitamin A.

5. The multi-vitamin and mineral supplement of claim 1 wherein the multi-vitamin and mineral supplement is comprised of about 10,000 I.U. of vitamin A.

6. The multi-vitamin and mineral supplement of claim 1 wherein the multi-vitamin and mineral supplement is comprised of about 1000 mg of vitamin C.

7. The multi-vitamin and mineral supplement of claim 1 wherein the multi-vitamin and mineral supplement is comprised of about 2000 mg of vitamin C.

8. The multi-vitamin and mineral supplement of claim 1 wherein vitamin E is in the form of d-alpha tocopherol succinate.

9. The multi-vitamin and mineral supplement of claim 1 wherein the multi-vitamin and mineral supplement is comprised of about 800 I.U of vitamin E.

10. The multi-vitamin and mineral supplement of claim 1 wherein the multi-vitamin and mineral supplement is comprised of about 1200 I.U. of vitamin E.

11. The multi-vitamin and mineral supplement of claim 1 wherein B3 is in the form of niacinamide.

12. The multi-vitamin and mineral supplement of claim 1 wherein vitamin B6 is in the form of pyridoxine hydrochloride.

13. The multi-vitamin and mineral supplement of claim 1 wherein vitamin B12 is in the form of cyanocobalamin.

14. The multi-vitamin and mineral supplement of claim 1 wherein the biotin is d-biotin.

15. The multi-vitamin and mineral supplement of claim 1 wherein the pantothenic acid is d-calcium pantothenate.

16. The multi-vitamin and mineral supplement of claim 1 wherein the pharmaceutically acceptable iron compound is selected from the group consisting of ferrous fumarate, ferrous sulfate, iron carbonyl, ferrous gluconate, ferrous chloride, ferrous lactate, ferrous tartrate, ferrous succinate, ferrous glutamate, ferrous citrate, ferrous pyrophosphate, ferrous cholinisocitrate, ferrous carbonate, iron-sugar-carboxylate complexes, and combinations thereof.

17. The multi-vitamin and mineral supplement of claim 16 wherein the pharmaceutically acceptable iron compound is iron carbonyl.

18. The multi-vitamin and mineral supplement of claim 1 wherein the multi-vitamin and mineral supplement is substantially free of iron.

19. The multi-vitamin and mineral supplement of claim 1 wherein the multi-vitamin and mineral supplement is comprised of about 18 mg of a pharmaceutically acceptable iron compound.

20. The multi-vitamin and mineral supplement of claim 1 wherein the pharmaceutically acceptable iodine compound is selected from the group consisting of potassium iodide, sodium iodide, and combinations thereof.

21. The multi-vitamin and mineral supplement of claim 20 wherein the pharmaceutically acceptable iodine compound is potassium iodide.

22. The multi-vitamin and mineral supplement of claim 1 wherein the pharmaceutically acceptable magnesium compound is selected from the group consisting of magnesium stearate, magnesium carbonate, magnesium oxide, magnesium hydroxide, magnesium sulfate, and combinations thereof.

23. The multi-vitamin and mineral supplement of claim 22 wherein the pharmaceutically acceptable magnesium compound is magnesium oxide.

24. The multi-vitamin and mineral supplement of claim 1 wherein the pharmaceutically acceptable zinc compound is selected from the group consisting of zinc sulfate, zinc chloride, zinc oxide, and combinations thereof.

25. The multi-vitamin and mineral supplement of claim 24 wherein the pharmaceutically acceptable zinc compound is zinc oxide.

26. The multi-vitamin and mineral supplement of claim 1 wherein the multi-vitamin and mineral supplement is comprised of about 100 mcg of selenium.

27. The multi-vitamin and mineral supplement of claim 1 wherein the multi-vitamin and mineral supplement is comprised of about 200 mcg of selenium.

28. The multi-vitamin and mineral supplement of claim 1 wherein the pharmaceutically acceptable copper compound is selected from the group consisting of cupric oxide, cupric sulfate, cupric gluconate, and combinations thereof.

29. The multi-vitamin and mineral supplement of claim 28 wherein the pharmaceutically acceptable copper compound is cupric gluconate.

30. The multi-vitamin and mineral supplement of claim 1 wherein the pharmaceutically acceptable chromium compound is selected from the group consisting of yeast-bound chromium, GTF chromium, niacin-bound chromium, and combinations thereof.

31. The multi-vitamin and mineral supplement of claim 30 wherein the pharmaceutically acceptable chromium compound is chromium amino acid chelate.

32. The multi-vitamin and mineral supplement of claim 1 wherein the pharmaceutically acceptable potassium compound is selected from the group consisting of potassium chloride, potassium glycerophosphate, potassium citrate, potassium gluconate, and potassium phosphate.

33. The multi-vitamin and mineral supplement of claim 32 wherein the pharmaceutically acceptable potassium compound is potassium phosphate.

34. The multi-vitamin and mineral supplement of claim 1 wherein the choline is choline bitartrate.

35. The multi-vitamin and mineral supplement of claim 1 wherein co-enzyme Q-10 is ubiquinone.

36. The multi-vitamin and mineral supplement of claim 1 wherein the supplement is further comprised of a pharmaceutically acceptable carrier material.

37. The multi-vitamin and mineral supplement of claim 1 which is administered orally once per day.

38. The multi-vitamin and mineral supplement of claim 1 wherein the total daily dosage is divided and administered in portions during the day.

39. The multi-vitamin and mineral supplement of claim 1 wherein the dosage form is enteric coated and compressed into a tablet or filled into hard of soft gelatin capsules.

* * * * *